US 8,467,047 B2

(12) United States Patent
Chen et al.

(10) Patent No.: US 8,467,047 B2
(45) Date of Patent: Jun. 18, 2013

(54) SYSTEMS AND METHODS FOR DETECTING DEFECTS ON A WAFER

(75) Inventors: Lu Chen, Sunnyvale, CA (US); Jason Kirkwood, Santa Clara, CA (US); Mohan Mahadevan, Livermore, CA (US); James A. Smith, Los Altos, CA (US); Lisheng Gao, Morgan Hill, CA (US); Junqing (Jenny) Huang, Fremont, CA (US); Tao Luo, Fremont, CA (US); Richard Wallingford, San Jose, CA (US)

(73) Assignee: KLA-Tencor Corp., San Jose, CA (US)

( * ) Notice: Subject to any disclaimer, the term of this patent is extended or adjusted under 35 U.S.C. 154(b) by 0 days.

(21) Appl. No.: 13/541,579

(22) Filed: Jul. 3, 2012

(65) Prior Publication Data
US 2012/0268735 A1    Oct. 25, 2012

Related U.S. Application Data

(62) Division of application No. 12/359,476, filed on Jan. 26, 2009, now Pat. No. 8,223,327.

(51) Int. Cl.
*G01N 21/00* (2006.01)
(52) U.S. Cl.
USPC .................................. 356/237.2; 356/237.3
(58) Field of Classification Search
USPC ... 356/237.1–237.6, 73; 438/14–18; 382/145, 382/141
See application file for complete search history.

(56) References Cited

U.S. PATENT DOCUMENTS

| 7,659,975 | B1 | 2/2010 | Ramani et al. |
| 8,126,255 | B2 | 2/2012 | Bhaskar et al. |
| 2004/0061850 | A1 | 4/2004 | Fisch et al. |
| 2004/0252879 | A1 | 12/2004 | Tiemeyer et al. |
| 2005/0110986 | A1 | 5/2005 | Nikoonahad et al. |
| 2008/0032429 | A1 | 2/2008 | Chen et al. |
| 2008/0273193 | A1 | 11/2008 | Nishiyama et al. |
| 2009/0080759 | A1 | 3/2009 | Bhaskar et al. |

FOREIGN PATENT DOCUMENTS

| JP | 2008-241716 | 10/2008 |
| RU | 2305320 | 8/2007 |
| WO | 99/67626 | 12/1999 |
| WO | 2007092950 | 8/2007 |

OTHER PUBLICATIONS

International Search Report and Written Opinion for PCT/US2010/021850 mailed Jul. 29, 2012.
International Search Report and Written Opinion for PCT/US2012/048324 mailed Oct. 18, 2012.

*Primary Examiner* — Tri T Ton
(74) *Attorney, Agent, or Firm* — Ann Marie Mewherter

(57) ABSTRACT

Systems and methods for detecting defects on a wafer are provided. One method includes generating output for a wafer by scanning the wafer with an inspection system using first and second optical states of the inspection system. The first and second optical states are defined by different values for at least one optical parameter of the inspection system. The method also includes generating first image data for the wafer using the output generated using the first optical state and second image data for the wafer using the output generated using the second optical state. In addition, the method includes combining the first image data and the second image data corresponding to substantially the same locations on the wafer thereby creating additional image data for the wafer. The method further includes detecting defects on the wafer using the additional image data.

17 Claims, 4 Drawing Sheets

SYSTEMS AND METHODS FOR DETECTING DEFECTS ON A WAFER

CROSS-REFERENCE TO RELATED APPLICATIONS

This application is a divisional of U.S. patent application Ser. No. 12/359,476 entitled "Systems and Methods for Detecting Defects on a Wafer," filed Jan. 26, 2009, which is incorporated by reference as if fully set forth herein.

BACKGROUND OF THE INVENTION

1. Field of the Invention

The present invention generally relates to systems and methods for detecting defects on a wafer. Certain embodiments relate to a method that includes combining different image data for substantially the same locations on the wafer generated using different optical states of an inspection system to create additional image data that is used to detect defects on the wafer.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor water. Additional examples of semiconductor fabrication processes include, but are not limited to, chemical-mechanical polishing (CMP), etch, deposition, and on implantation. Multiple semiconductor devices may be fabricated in an arrangement on a single semiconductor wafer and then separated into individual semiconductor devices.

Inspection processes are used at various steps during a semiconductor manufacturing process to detect defects on wafers to promote higher yield in the manufacturing process and thus higher profits. Inspection has always been an important part of fabricating semiconductor devices such as ICs. However, as the dimensions of semiconductor devices decrease, inspection becomes even more important to the successful manufacture of acceptable semiconductor devices because smaller defects can cause the devices to fail. For instance, as the dimensions of semiconductor devices decrease, detection of defects of decreasing size has become necessary since even relatively small defects may cause unwanted aberrations in the semiconductor devices.

One obvious way to improve the detection of relatively small defects is to increase the resolution of an optical inspection system. One way to increase the resolution of an optical inspection system is to decrease the wavelength at which the system can operate. As the wavelength of inspection systems decreases, incoherent light sources are incapable of producing light with sufficient brightness. Accordingly, for inspection systems that are designed to operate at smaller wavelengths, a more suitable light source is a laser light source that can generate relatively bright light at relatively small wavelengths. However, laser light sources generate coherent light. Such light is disadvantageous for inspection since coherent light can produce speckle in images of a wafer. Since speckle is a source of noise in the images, the signal-to-noise ratio (S/N) images generated by inspection systems will be reduced by speckle. In addition, speckle noise in wafer inspection systems (e.g., laser-based inspection systems) is one of the main limitations of defect of interest (DOI) detection ability. As wafer design rules continue to shrink, optical inspection systems preferably have shorter wavelengths and larger collection numerical apertures (NAs). Speckle noise consequently increases to a more dominant noise source.

Many illumination systems have been developed for inspection applications that reduce the speckle of light from laser light sources. For example, popular approaches to reduce speckle noise currently involve reducing coherence of the illumination laser source by transmitting light through an optical diffuser or vibrating optical fiber. These approaches usually require increasing the illumination NA on the wafer and therefore are not effective for an outside-the-lens (OTL) oblique angle illumination architecture. Reduction of laser coherence also limits the usage of Fourier filtering and degrades the S/N. Other approaches such as moving an aperture in the pupil plane have been applied to select a spatial sample of light in the pupil plane and then average the image over a relatively large number of samples. This approach will greatly reduce the resolution of the optical system thereby decreasing the defect capture rate.

Some methods for defect detection utilize output generated by multiple detectors of an inspection system to detect defects on a wafer and/or to classify defects detected on the wafer. Examples of such systems and methods are illustrated in International Publication No. WO 99/67626 by Ravid et al., which is incorporated by reference as if fully set forth herein. The systems and methods described in this publication are generally configured to separately detect defects in the electrical signals produced by different detectors. In other words, the electrical signals produced by each of the detectors are processed separately to determine if each detector has detected a defect. At any time that a defect is detected in the electrical signals produced by one of the detectors, the electrical signals produced by at least two of the detectors are analyzed collectively to determine scattered light attributes of the defect such as reflected light intensity, reflected light volume, reflected light linearity, and reflected light asymmetry. The defect is then classified (e.g., as a pattern defect or a particle defect) based on these attributes.

Although the methods and systems disclosed in the above-referenced publication utilize scattered light attributes of defects determined from electrical signals generated by more than one detector, the methods and systems disclosed in this publication do not utilize electrical signals generated by more than one detector in combination to detect the defects. In addition, the methods and systems disclosed in this publication do not use a combination of electrical signals generated by more than one detector for any defect-related function other than classification.

Other currently available inspection systems are configured to inspect a wafer with more than one detection channel, to detect defects on the wafer by separately processing the data acquired by each of the channels, and to classify the defects by separately processing the data acquired by each of the channels. The defects detected by each of the individual channels may also be further processed separately, for example, by generating different wafer maps, each illustrating the defects detected by only one of the individual channels. The defect detection results generated by more than one channel of such a system may then be combined using, for example, Venn addition of the individual wafer maps. Such inspection may also be performed using output acquired in a single pass or multiple passes. For example, one previously used method for defect detection includes performing two or more scans of a wafer and determining the union of the lot results as the final inspection result for the wafer. In such previously used methods, nuisance filtering and defect binning is based on the Venn ID results, AND/OR operation, from multiple scans.

Such previously used inspection methods, therefore, do not leverage the output generated by the inspection system at the pixel level, but rather combine the results at the wafer map level as the final result. Defects are detected by each pass independently based on their relative signal (magnitude) compared to the wafer level noise seen for each pass. In addition, nuisance filtering and binning in previously used methods may be based on the AND/OR detection from multiple scans and thereafter separation in each individual scan. As such, no cross-pass information other than the AND/OR operation on detection is considered.

Accordingly, it would be advantageous to develop methods and systems for detecting defects on a wafer that combine information from different optical states of an inspection system to increase the S/N of defects in image data for the wafer used for defect detection while decreasing noise (e.g., speckle noise) in the image data.

SUMMARY OF THE INVENTION

The following description of various embodiments of methods, computer readable media, and systems is not to be construed in any way as limiting the subject matter of the appended claims.

One embodiment relates to a method for detecting defects on a wafer. The method includes generating output for a wafer by scanning the wafer with an inspection system using first and second optical states of the inspection system. The first and second optical states are defined by different values for at least one optical parameter of the inspection system. The method also includes generating first image data for the wafer using the output generated using the first optical state and second image data for the wafer using the output generated using the second optical state. In addition, the method includes combining the first image data and the second image data corresponding to substantially the same locations on the wafer thereby creating additional image data for the wafer. The method further includes detecting defects on the wafer using the additional image data.

In one embodiment, the different values include different angles of illumination at which light is directed to the wafer during the scanning. In another embodiment, scanning the wafer with the inspection system using the first and second optical states is performed with coherent light. In an additional embodiment, the first and second optical states are defined by the same values for optical parameters of the inspection system used for collecting light from the wafer during the scanning. In a further embodiment, the different values include different imaging modes, different polarization states, different wavelengths, different pixel sizes, or some combination thereof. In another embodiment, the different values include different channels of the inspection system. In one such embodiment, generating the output using the first and second optical states is performed in parallel.

In one embodiment, generating the output is performed in one pass. In one such embodiment, the method also includes generating additional output for the wafer by scanning the wafer in a different pass with the inspection system using the first or second optical state of the inspection system, generating different image data for the wafer using the additional output generated in the different pass, combining the different image data with the first image data if the different pass is performed using the first optical state or the second image data if the different pass is performed using the second optical state corresponding to substantially the same locations on the wafer thereby creating further additional image data for the wafer, and detecting defects on the wafer using the further additional image data.

In another embodiment, the method includes generating output for the wafer by scanning the wafer with a different inspection system, generating third image data for the wafer using the output generated using the different inspection system, combining the third image data with the first or second image data corresponding to substantially the same locations on the wafer thereby creating further additional image data for the wafer, and detecting defects on the wafer using the further additional image data.

In one embodiment, the first and second image data includes difference image data. In another embodiment, combining the first image data and the second image data includes performing image correlation on the first image data and the second image data corresponding to substantially the same locations on the wafer. In an additional embodiment, combining the first image data and the second image data is performed at the pixel level of the first and second image data. In a further embodiment, defect detection is not performed prior to the combining step.

In one embodiment, portions of the additional image data that correspond to the defects have greater signal-to-noise ratios than portions of the first and second image data that are combined to create the portions of the additional image data. In another embodiment, the additional image data has less noise than the first and second image data. In an additional embodiment, the additional image data has less speckle noise than the first and second image data. In a further embodiment, the method includes detecting defects on the wafer using the first image data, detecting defects on the wafer using the second image data, and reporting the defects detected on the wafer as a combination of the defects detected using any of the first image data, the second image data, and the additional image data.

In one embodiment, the method includes determining values for features of the defects using the additional image data. In another embodiment, the method includes determining values for features of the defects using some combination of the first image data, the second image data, and the additional image data.

In one embodiment, detecting the defects includes identifying potential defects on the wafer using the additional image data and identifying the defects by performing nuisance filtering of the potential defects using pixel level information about the potential defects determined using the first image data, the second image data, the additional image data, or some combination thereof. In another embodiment, detecting the defects includes identifying potential defects on the wafer using the additional image data and identifying the defects by performing nuisance filtering of the potential defects using values for features of the defects determined using the first image data, the second image data, the additional image data, or some combination thereof.

In one embodiment, the method includes binning the defects using pixel level information about the defects determining using the first image data, the second image data, the additional image data, or some combination thereof. In another embodiment, the method includes binning the defects using values of features of the defects determined using the first image data, the second image data, the additional image data, or some combination thereof.

Each of the steps of each of the embodiments of the method described above may be further performed as described herein. In addition, each of the embodiments of the method described above may include any other step(s) of any other method(s) described herein. Furthermore, each of the embodiments of the method described above may be performed by any of the systems described herein.

Another embodiment relates to a computer-readable medium that includes program instructions executable on a computer system for performing a computer-implemented method for detecting defects on a wafer. The method includes acquiring output for a wafer generated by scanning the wafer with an inspection system using first and second optical states of the inspection system. The first and second optical states are defined by different values for at least one optical parameter of the inspection system. The method also includes generating first image data for the wafer using the output generated using the first optical state and second image data for the wafer using the output generated using the second optical state. In addition, the method includes combining the first image data and the second image data corresponding to substantially the same locations on the wafer thereby creating additional image data for the wafer. The method further includes detecting defects on the wafer using the additional image data.

Each of the steps of the computer-implemented method described above may be further performed as described herein. In addition, the computer-implemented method may include any other step(s) of any other method(s) described herein. The computer-readable medium may be further configured as described herein.

An additional embodiment relates to a system configured to detect defects on a wafer. The system includes an inspection subsystem configured to generate output for a wafer by scanning the wafer using first and second optical states of the inspection subsystem. The first and second optical states are defined by different values for at least one optical parameter of the inspection subsystem. The system also includes a computer subsystem configured to generate first image data for the wafer using the output generated using the first optical state and second image data for the wafer using the output generated using the second optical state. The computer subsystem is also configured to combine the first image data and the second image data corresponding to substantially the same locations on the wafer thereby creating additional image data for the wafer. In addition, the computer subsystem is configured to detect defects on the wafer using the additional image data. The system may be further configured as described herein.

A further embodiment relates to another method for detecting defects on a wafer. This method includes generating output for a wafer by scanning the wafer with an inspection system in first and second passes using a first optical state of the inspection system. The method also includes generating first image data for the wafer using the output generated in the first pass and second image data for the wafer using the output generated in the second pass. In addition, the method includes combining the first image data and the second image data corresponding to substantially the same locations on the wafer thereby creating additional image data for the wafer. The method further includes detecting defects on the wafer using the additional image data.

Each of the steps of the method described above may be further performed as described herein. In addition, the method described above may include any other step(s) of any other method(s) described herein. Furthermore, the method described above may be performed by any of the systems described herein.

Still another embodiment relates to another method for detecting defects on a wafer. This method includes generating output for a wafer by scanning the wafer with first and second inspection systems. The method also includes generating first image data for the wafer using the output generated using the first inspection system and second image data for the wafer using the output generated using the second inspection system. In addition, the method includes combining the first image data and the second image data corresponding to substantially the same locations on the wafer thereby creating additional image data for the wafer. The method further includes detecting defects on the wafer using the additional image data.

Each of the steps of the method described above may be further performed as described herein. In addition, the method described above may include any other stem's) of any other method(s) described herein. Furthermore, the method described above may be performed by any of the systems described herein.

BRIEF DESCRIPTION OF THE DRAWINGS

Further advantages of the present invention may become apparent to those skilled in the art with the benefit of the following detailed description of the preferred embodiments and upon reference to the accompanying drawings in which.

Figure 1:
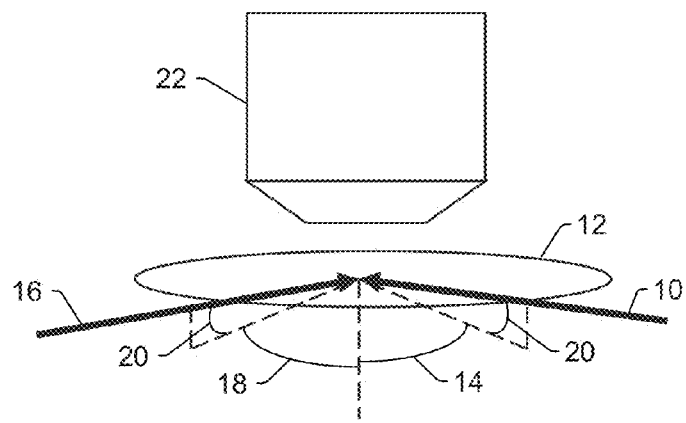
FIG. 1 is a schematic diagram illustrating a side view of one embodiment of different optical states of an inspection system that are defined by different values for at least one optical parameter of the inspection system.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

One or more layers may be formed upon a wafer. Many different types of such layers are known in the art, and the term wafer as used herein is intended to encompass a wafer on which all types of such layers may be formed. One or more layers formed on a wafer may be patterned. For example, a wafer may include a plurality of dies, each having repeatable patterned features. Formation and processing of such layers of material may ultimately result in completed semiconductor devices. As such, a wafer may include a substrate on which not all layers of a complete semiconductor device have been formed or a substrate on which all layers of a complete semiconductor device have been formed.

The wafer may further include at least a portion of an integrated circuit (IC), a thin-film head die, a micro-electromechanical system (MEMS) device, fiat panel displays, magnetic heads, magnetic and optical storage media, other components that may include photonics and optoelectronic devices such as lasers, waveguides and other passive components processed on wafers, print heads, and bio-chip devices processed on wafers.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

One embodiment relates to a method for detecting defects on a wafer. The method includes generating output for a wafer by scanning the wafer with an inspection system using first and second optical states of the inspection system. The output generated by scanning the wafer may include any suitable output and may vary depending on the configuration of the inspection system and/or the inspection recipe used to perform the scanning. For example, the output may include signals, data, images, or image data responsive to light scattered from the wafer (e.g., in the case of dark field (DF) inspection systems).

The inspection system may be a commercially available inspection system such as the Puma 91xx series tools, which are commercially available from KLA-Tencor, San Jose, Calif. The inspection system may be configured for inspection of patterned wafers and/or unpatterned wafers. In addition, the inspection system may be configured for DF inspection, possibly in combination with one or more other inspection modes (e.g., an aperture mode of inspection). Furthermore, the inspection system may be configured as an optical inspection system. Scanning the wafer with the inspection system may be performed in any suitable manner. For example, the wafer may be moved (by a stage of the inspection system) with respect to optics of the inspection system such that the illumination of the inspection system traces a serpentine path over the wafer as light scattered from the wafer is detected.

The first and second optical states are defined by different values for at least one optical parameter of the inspection system. For example, an optical "state" (which may also be commonly referred to as an optical "configuration" or "mode") of the inspection system can be defined by values for different optical parameters of the inspection system that are or can be used in combination to generate output for a wafer. The different optical parameters may include, for example, wavelength of illumination, wavelength of collection/detection, polarization of illumination, polarization of collection/detection, illumination angle (defined by elevation angle or angle of incidence and possibly azimuthal angle), angle of collection/detection, pixel size, and the like. The first and second optical states may be defined by different values for only one of the optical parameters of the inspection system and the same values for other optical parameters of the inspection system. However, the first and second optical states may be defined by different values for two or more of the optical parameters of the inspection system.

In one embodiment, the different values include different angles of illumination at which light is directed to the wafer during the scanning. The different angles of illumination may include substantially the same elevation angle and different azimuthal angles. FIG. 1 illustrates one such embodiment of different optical states of an inspection system that are defined by different values for at least one optical parameter of the inspection system. For example, as shown in FIG. 1, light 10 may be directed to wafer 12 at azimuthal angle 14 (e.g., an azimuthal angle of about 45 degrees). Light 16 may be directed to the wafer at azimuthal angle 18 (e.g., an azimuthal angle of about −45 degrees). Light 10 and light 16 may be directed to the wafer at the same or substantially the same elevation angle 20 (e.g., about 15 degrees). However, light 10 and light 16 may be directed to the wafer at different elevation angles and/or different azimuthal angles. Light 10 and light 16 may be generated by different light sources or the same light source.

Light 10 and light 16 may have substantially the same characteristics (e.g., wavelength, polarization, etc.). In this manner, in order to separately detect the light scattered from the wafer due to illumination at the different illumination angles to thereby generate separate output for the different optical states, the wafer may be scanned with light at the different illumination angles in different passes (i.e., multiple passes performed in a single process). For example, in a double pass inspection, first pass output may be generated with illumination coming in at a certain elevation angle and a 45 degree azimuthal angle. Second pass output may be generated with the same optical conditions used for the first pass except at −45 degree azimuthal angle illumination.

Such multiple pass (or multi-pass) output generation may be performed for any different optical states of the inspection system for which output cannot be simultaneously and separately generated (e.g., due to a difference in a setting of a single optical element of the inspection system between the different optical states). However, if the different optical states of the inspection system can be used to simultaneously generate separate output for the wafer using different channels of the inspection system), then generating the output using the first and second optical states of the inspection system may be performed in a single pass scan of the wafer.

In another embodiment, scanning the wafer with the inspection system using the first and second optical states is performed with coherent light. The coherent light may include light generated by any suitable coherent light source (e.g., a laser) at any suitable wavelength. In addition, the method may be performed using an outside-the-lens (OTL) optical inspection system in which the illumination source is laser light incident on the wafer at an oblique angle of incidence. In one such embodiment, as shown in FIG. 1, light 10 and light 16 may be directed to the wafer at an oblique angle of incidence and outside of lens 22 of the inspection system. Lens 22 may be configured to collect light scattered from the wafer due to illumination of the wafer during scanning. An inspection system that includes lens 22 may be further configured as described herein.

In this manner, one advantage of the embodiments described herein is that the embodiments can reduce speckle noise as described further herein; and compared to other common approaches for reducing speckle noise, the coherence of the laser source may be preserved. Therefore, in the embodiments described herein, a Fourier filtering technique can be applied effectively to eliminate pattern background in a DF geometry. The Fourier filtering technique may include any (optical or data processing) Fourier filtering technique known in the art. Although the output may be advantageously generated in the embodiments described herein by scanning the wafer using coherent light in an OIL illumination configuration, the output may be generated using any suitable light in any suitable illumination configuration.

In an additional embodiment, the first and second optical states are defined by the same values for optical parameters of the inspection system used for collecting light from the wafer during the scanning. For example, as described above, the values may include different angles of illumination at which light is directed to the wafer during scanning. In addition, the different optical states may be different only in one or more illumination optical parameters of the inspection system. As such, no change in collection optical path between the different optical states (using which output may be generated in possibly different passes or scans of the wafer) may be made since only the illumination may be changed. Using the same collection optical path for the different optical states may advantageously reduce the alignment error and optical error between different image data, which may be generated as described herein using output acquired by scanning the wafer in two or more passes) and which may be combined as described further herein.

In a further embodiment, the different values include different imaging modes, different polarization states, different wavelengths, different pixel sizes, or some combination thereof. For example, the different values may include different polarization states for illumination. In one such example, the first and second optical states may be defined by the same polarization states for collection. For example, the different values may include the p-polarized (P) state for illumination in one optical state and the s-polarized (S) state for illumination in the other optical state, and the polarization state used for collection in both optical states may be unpolarized (N). However, in another such example, the optical states may also be defined by different polarization states for collection. For example, the first optical state may be defined by the S polarization state for illumination and the P polarization state for collection, and the second optical state may be defined by the P polarization state for illumination and the S polarization state for collection.

In another embodiment, the different values include different channels of the inspection system. For example, the first optical state may be defined by a first channel of the inspection system, and the second optical state may be defined by a second channel of the inspection system. In other words, the output for the wafer may be generated for the first optical state using one channel of the inspection system, and the output for the wafer may be generated for the second optical state using a different channel of the inspection system. The term "channel" is generally used herein to refer to different detection subsystems or detectors of the inspection system, which may be different in angles (i.e., collection angles) at which light from the wafer is collected and detected by the detection subsystems or detectors, but which may or may not be different in other respects as well (e.g., wavelength(s) at which light is detected by the channels, polarization of the light detected by the channels, etc.).

In one such example, if the inspection system includes three channels, the first and second optical states may be defined by the following channel combinations: channel 1 and channel 2; channel 2 and channel 3; and channel 1 and channel 3. In addition, as described further herein, the embodiments may be performed using more than two different optical states. In one such example, if the inspection system includes three channels, first, second, and third optical states may be defined by channel 1, channel 2, and channel 3, respectively. Furthermore, each of the different optical states may be defined by a different channel of the inspection system (e.g., N optical states defined by N channels).

In one such embodiment, generating the output using the first and second optical states is performed in parallel. For example, the output generated using the first and second optical states may be generated in the same pass or scan. As such, the output from each channel may be collected in parallel.

The method also includes generating first image data for the wafer using the output generated using the first optical state and second image data for the wafer using the output generated using the second optical state. In one embodiment, the first and second image data includes difference image data. The difference image data may be generated in any suitable manner. For example, difference image data for the first optical state may be generated using test image data and two references (e.g., image data from dies on the wafer that are adjacent to the die from which the test image data was generated). In such an example, one reference may be subtracted from the test image data, and the other reference may be separately subtracted from the test image data. The results of both subtraction operations may be multiplied, and the absolute value of that product may be the difference image data. Difference image data for the second optical state may be generated in a similar manner. As such, the difference image data may be separately generated for each optical state using only output generated using that optical state. In other words, generating the difference image data is not a cross-optical state operation. In this manner, generating the first and second image data may include performing a die-to-die subtraction to eliminate pattern background in the output. However, the difference image data may be generated in any other suitable manner using any suitable algorithm(s) and/or method(s). In addition, the first and second image data may not be difference image data. For example, the first and second image data may be raw image data of the wafer after any other pattern background elimination operation(s) (e.g., after Fourier filtering).

The method also includes combining the first image data and the second image data corresponding to substantially the same locations on the wafer thereby creating additional image data for the wafer. In this manner, the first and second image data may be combined on a location-to-location basis. Unlike other methods that involve combining information about a wafer acquired using different optical states of an inspection system, combining the first image data and the second image data as described herein creates different image data for the wafer, which can then be used as described further herein (e.g., for defect detection). For example, combining the first and second image data may include performing "image fusion" using the first image data and the second image data. In other words, new image data of the wafer may be "fused" from two other image data of the wafer. As such, image fusion may be performed using multiple optical states, which may include any of those described herein (e.g., optical states defined by different polarizations, different channels, etc.). For example, image fusion can be achieved by using image data from any two (or more) channels of the inspection system, in one such example, if the inspection system includes three channels, image fusion can be performed using the following channel combinations: channel 1 and channel 2; channel 2 and channel 3; channel 1 and channel 3; and channels 1, 2, and 3. In addition, as described further herein, the output used to generate the first image data and the second image data may be acquired in different passes. In this manner, the method may include multi-pass image fusion. However, as also described further herein, the output used to generate the first and second image data may be acquired in a single pass (e.g., output from each channel may be collected in parallel). As such, the method may include single-pass image fusion.

Although the method includes combining the first image data and the second image data as described above, the method is not limited to combining only the first image data and the second image data. For example, if output is generated for the wafer using a third optical state of the inspection system, which is defined by at least one value for at least one optical parameter of the inspection system that is different than the values for that at least one optical parameter which define the first and second optical states, the method may include generating third image data for the wafer using the output generated using the third optical state, which may be performed as described herein. The third optical state may be defined by any of the different values for any of the optical parameters described herein. In one such example, each of the different optical states may be defined by a different channel of the inspection system. The method may also include combining the first image data, the second image data, and the third image data corresponding to substantially the same locations on the wafer as described herein thereby creating the additional image data for the wafer. Combining image data generated using output generated by two or more optical states is advantageous as described further herein.

Furthermore, although the method includes creating additional image data for the wafer, the method is not limited to creating only the additional image data for the wafer. For example, the method may include creating the additional image data for the wafer as described above and creating different additional image data for the wafer in a similar manner. In one such example, the additional image data may be created by combining the first and second image data as described above. The method may also include generating output for the wafer using a third optical state of the inspection system, which may be defined as described further herein. That output may be used to generate third image data for the wafer as described further herein. That third image data may then be combined as described herein with the first image data and/or the second image data to create different additional image data. The different additional image data may be used in a manner similar to using the additional image data in steps described further herein.

In one embodiment, combining the first image data and the second image data includes performing image correlation on the first image data and the second image data corresponding to substantially the same locations on the wafer. For example, new wafer image data or the fused image data may be generated by correlating image data (e.g., from two passes). In one example, the image correlation may include a 5 pixel by 5 pixel correlation. However, the image correlation may be performed in any other suitable manner using any suitable image correlation algorithm(s) and/or method(s). In addition, the image correlation may be performed using any suitable image processing technique that can be used for image correlation.

In another embodiment, combining the first image data and the second image data is performed at the pixel level of the first and second image data. In other words, the first and second image data may be combined on a pixel-by-pixel basis. In still other words, combining the first and second image data may be performed separately for individual pixels in the first and second image data. By fusing information at the pixel level, one can leverage both magnitude (intensity) and phase (correlation) information among different optical states (which may be generated by different inspection passes). By combining information at the pixel level, a new dimension to exploit becomes available, namely the coincidence among different perspectives (optical states).

The first and second image data (e.g., difference image data) for the different optical states may be generated for the entire wafer or the entire portion of the wafer that is scanned with the inspection system using the first and second optical states. In addition, combining the first and second image data may be performed using all of the first and second image data. In this manner, image fusion may be performed for the entire wafer or the entire portion of the wafer that is scanned using the first and second optical states.

However, image fusion may not be performed for the entire wafer or the entire scanned portion of the wafer. For example, the method may include applying an intensity cut off to the first and/or second image data and eliminating any of the first and/or second image data that does not have intensity values that exceed the intensity cut off. In this manner, the first and/or second image data that is not eliminated may be identified as candidates to be used for additional steps performed in the method. In one such example, if the first image data is generated using output generated in a first pass of the wafer and the second image data is generated using output generated in a second pass of the wafer, the intensity cut off may be applied to the first image data to eliminate any of the first image data that does not have intensity values that exceed the intensity cut off. In this manner, the method may include saving image patch data for only the candidates identified in the first pass. In the second pass, only second image data that corresponds to the same locations on the wafer as the candidates may be stored and/or combined with the first image data. In this manner, the image data that is saved in the second pass may vary depending on the candidates that were captured in the first pass, and image fusion may then be performed using the image data saved in the second pass. However, if the first and second image data is generated using output that is generated in a single pass of the wafer, the intensity cut off may be applied to both the first and second image data and any of the first and second image data that has values that exceed the intensity cut off may be combined with the corresponding image data regardless of the intensity values of that other image data.

The method may include performing some (i.e., one or more) dilation steps to ensure proper alignment between the defect signals in the image data. For example, for each of the candidates identified as described above, a 3 pixel by 3 pixel dilation may be performed. However, the dilation stem's) may include any suitable dilation image processing technique(s) known in the art and may be performed using any suitable method(s) and/or algorithm(s). The dilation step(s) may be performed on both the first and second image data thereby increasing the accuracy with which defect signals in the first and second image data are aligned to each other.

Regardless of whether or not the method includes dilation step(s) such as those described above, the method may include aligning the first and second image data prior to the combining step. Image data alignment may be performed in any suitable manner. For example, image data alignment may be performed through cross-correlation of X and Y projections (e.g., of the average intensity across the image data in the x and y directions) between image data generated for different optical states (e.g., from image data acquired in two passes).

In an additional embodiment, defect detection is not performed prior to the combining step. For example, as described above, an intensity cut off may be applied to the first and/or second image data prior to the combining step. However, the intensity cut off is not a defect detection threshold, method, or algorithm. Instead, the intensity cut off acts essentially as a noise filter to eliminate the image data that does not have relatively high intensity values only for the purpose of decreasing the processing involved in other steps of the method. In addition, defect detection may be performed as described further herein using the first and second image data individually, and defect detection using the first and/or second image data may or may not be performed prior to performing the combining step. However, defect detection cannot be performed using the additional image data until after the combining step in which the additional image data is created has been performed. In this manner, unlike methods and systems that involve combining information generated after defect detection (e.g., combining defect detection results from different scans of a wafer), the embodiments described herein combine information prior to defect detection, which is advantageous as described further herein.

Since the embodiments described herein include combining first and second image data to create additional image data, a fairly substantial amount of image data may be stored during the method. Examples of methods and systems that are particularly suitable for storing relatively large amounts of data such as image data are described in commonly owned U.S. patent application Ser. No. 12/234,201 by Bhaskar et al. filed Sep. 19, 2008, now U.S. Pat. No. 8,126,255 issued on Feb. 28, 2012, which is incorporated by reference as if fully set forth herein. The embodiments described herein may include storing the output and/or image data generated by the embodiments described herein using the methods and systems described in this patent application. For example, a system may include eight image computers. During the first pass of a multi-pass inspection performed with a first optical state, each image computer may receive and store ⅛ of the image data for each swath scanned on a wafer. During the second pass of the multi-pass inspection performed with a second optical state, each image computer may receive and store ⅛ of the image data for each swath scanned on the wafer. In addition, each image computer may receive and store image data generated at substantially the same locations on the wafer in both passes (i.e., image data generated at substantially the same wafer locations and/or substantially the same in-swath positions). The image data generated during the second pass may be stored in the image buffers of the image computers at fixed offset locations from the locations of the stored first pass image data. The stored image data may then be used in any of the step(s) described herein. The computer systems and computer subsystems described herein may be further configured as described in the above-referenced patent application. The embodiments described herein may also include any step(s) of any method(s) described in the above-referenced patent application.

The method further includes detecting defects on the wafer using the additional image data. Therefore, defect detection is no longer only determined by each optical state (or each pass) independently, but based on information fused from multiple optical states (e.g., all passes). In this manner, the methods described herein use image fusion results, which are generated by combining information from raw (difference) image data generated by multiple optical states, as the input to defect detection. The defects detected on the wafer using the additional image data may include any defects known in the art and may vary depending on one or more characteristics of the wafer (e.g., the wafer type or the process performed on the wafer prior to inspection).

Detecting the defects using the additional image data may include applying one or more defect detection thresholds to the additional image data. For example, the additional image data may be compared to one or more defect detection thresholds. The one or more defect detection thresholds can be used to make a decision regarding whether a pixel in the additional image data is defective or not. Other methods for defect detection using one or more defect detection thresholds may first select a set of candidate pixels using a simpler (less computationally involved) test followed by a more complex computation applied only to the candidates to detect defects.

One or more detect detection thresholds that are used to detect the defects on the wafer may be defect detection threshold(s) of one or more detect detection algorithms, which may be included in an inspection recipe. The one or more defect detection algorithms that are applied to the additional image data may include any suitable defect detection algorithm(s) and may vary depending on, for example, the type of inspection that is being performed on the wafer. Examples of suitable defect detection algorithms, which can be applied to the additional image data, include segmented auto-thresholding (SAT) or multiple die auto-thresholding (MDAT), which are used by commercially available inspection systems such as those from KLA-Tencor. In this manner, the additional image data may be treated as any other image data when it comes to defect detection.

In one embodiment, the additional image data has less noise than the first and second image data. For example, combining the image data for the wafer generated for different optical states as described herein offers new context of the noise profile of the wafer and sensitivity to defects of interest (DOI). In addition, by combining (or fusing) information from multiple optical states at the pixel level, the sensitivity to nuisance events or noise can be reduced. For example, by performing the image correlation as described above, wafer noise in the first image data and the second image data that is non-spatially coincident can be substantially eliminated in the additional image data. In this manner, the embodiments described herein leverage the fact that different optical states (e.g., defined by different imaging modes, polarization states, wavelengths, pixel sizes, etc.) provide different perspectives of the wafer level noise and nuisance defects thereby offering the potential to suppress noise in the additional image data, which may be used as described further herein (e.g., for defect detection purposes).

In an additional embodiment, the additional image data has less speckle noise than the first and second image data. For example, the embodiments described herein may use an image correlation process (to create the additional image data) thereby substantially eliminating un-correlated speckle noise. In addition, as described above, the first and second optical states may be defined by different illumination angles. As such, the embodiments described herein may be used for speckle noise suppression by varying illumination angle. In other words, the embodiments described herein may be used for speckle noise suppression by correlating image data generated using output that is generated using various illumination angles in an optical inspection system. For example, as the illumination angle changes, the phase relationship of the scattered light from the surface roughness on the wafer changes. The speckle pattern in the image data changes accordingly. When this change is sufficient, a correlation of different image data will help to eliminate the speckle noise.

Figure 2:
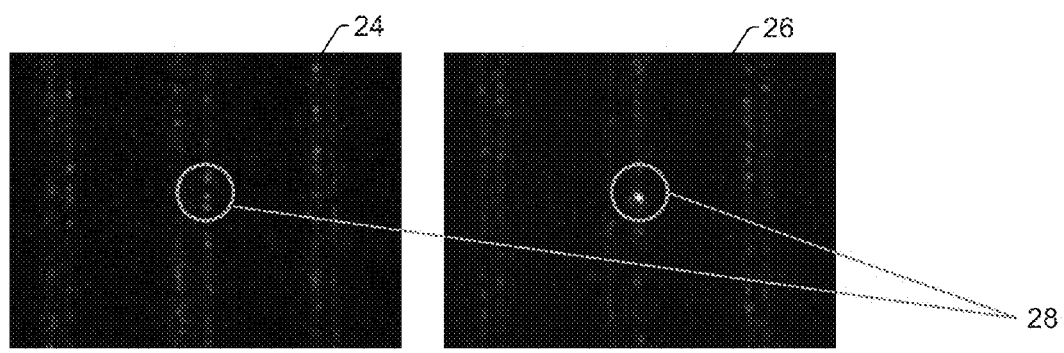
FIG. 2 includes different image data for the same location on a wafer, each of which was generated using output that was generated using one of the different optical states of FIG. 1.

An example of how the speckle pattern changes as illumination angle changes is shown in FIG. 2. inspection image data 24 and 26 was generated for the same location on a wafer. Inspection image data 24 was acquired at an illumination azimuthal angle of 45 degrees. Inspection image data 26 was acquired at an illumination azimuthal angle of −45 degrees. Therefore, the inspection image data was acquired at different illumination angles (e.g., the same elevation angle but different azimuthal angles). Portions 28 of the image data show that the speckle signatures produced by the two azimuthal angle illuminations are substantially different at the same location on a page break. In particular, the bright speckle spot in inspection image data 26 is caused by surface roughness and will contribute as noise or nuisance. In inspection image data 24, the bright speckle spot is not present at the same location as the speckle pattern changes with the illumination angle. Therefore, the wafer noise changes as the azimuthal angle of illumination changes. In particular, the bright speckle disappears as the azimuthal angle is changed from −45 degrees to 45 degrees.

In one embodiment, portions of the additional image data that correspond to defects on the wafer have greater signal-to-noise ratios (S/Ns) than portions of the first and second image data that are combined to create the portions of the additional image data. For example, by combining (or fusing) information from multiple optical states at the pixel level, weak signal strengths from may be enhanced. Enhancing the signal strengths from DOI may be achieved by not only taking advantage of the relative signals for defects in each optical state (magnitude), but by also exploiting coincidence or correlations among the different optical states (phase). For example, fusing information at the pixel level thereby leveraging both magnitude (intensity) and phase (correlation) information among different optical states allows one to extract defects with weak signals and suppress noise and nuisance events by exploiting their respective coincidence and non-coincidence for different optical states. In this manner, the embodiments described herein leverage the fact that different optical states (e.g., defined by different imaging modes, polarization states, wavelengths, pixel sizes, etc.) provide different perspectives of the wafer level noise and nuisance defects thereby offering the potential to enhance the contrast of the DOI and their separation from nuisance defects. In addition, pixel level image fusion across multiple optical states provides opportunities for enhancement of separation between DOI and nuisances although both may have relatively high S/Ns.

In one such example, when the change in the speckle pattern is sufficient between different optical states used to generate the output for the wafer, a correlation of different image data for the different optical states will help to eliminate the speckle noise and improve the S/N as the signal scattering intensity from the defect may be relatively constant. For example, if the illumination angles are symmetric in optical architecture, defect signals may be similar in both optical states, which is especially true for relatively small defects. While reducing speckle noise after image correlation, the defect signal is maintained during the process. In this manner, the embodiments described herein can maintain a healthy defect signal level after image correlation. For example, compared to other common approaches for reducing speckle noise, the speckle noise is selectively eliminated instead of averaging over a relatively large sample of speckle patterns. Selectively eliminating the speckle noise instead of averaging over a relatively large sample of speckle patterns helps to reduce the noise floor and improve the S/N.

In this manner, as the examples described herein illustrate, the defect S/N in the additional image data is greatly improved over the S/N of the defect in each individual optical state, especially on wafers where speckle noise is dominant. For example, a defect that is not detectable using either optical state (using either difference image data generated using one illumination angle) may become detectable after image correlation. In particular, one advantage of the embodiments described herein is that speckle noise can be greatly reduced in the additional image data compared to the first and second image data while defect S/Ns in the additional image data are improved compared to the first and second image data. As such, a defect that is not detectable in either of the first and second image data may become detectable in the corresponding additional image data created by image correlation.

However, the embodiments described herein can be used to increase the S/Ns for defects that are detectable in either one or both of the first and second image data individually (e.g., using image data from one illumination angle and/or using image data from a different illumination angle). For example, even if a defect produces a moderate S/N in one of the optical states defined by one illumination polarization state and a feeble S/N in another of the optical states defined by a different illumination polarization state, the defect S/N in the additional image data can be increased relative to both optical states because fusing the information from the two optical states can both suppress noise and enhance signal. In addition, if a detect produces marginal S/Ns in two optical states defined by different illumination polarization states, the defect S/N in the additional image data can be increased relative to both optical states.

Furthermore, if a defect produces appreciable S/Ns in two optical states defined by different illumination polarization states and different collection polarization states but noise (e.g., from the grain of the wafer) dominates the first and second image data, the noise can be significantly reduced in the additional image data compared to the first and second image data by combining the first and second image data as described herein. In a similar manner, if a defect has S/Ns in two optical states, defined by different illumination polarization states and different collection polarization states, that are on par with the maximum S/Ns of noise (e.g., from a grain signature) in the first and second image data, the noise can be significantly reduced in the additional image data compared to the first and second image data by combining the first and second image data as described herein.

In another example, different peak noise events may be present in first and second image data generated using first and second optical states defined by different channels of the inspection system, but a defect may have sufficient correlation in the first and second image data such that by combining the first and second image data as described herein, the S/N of the defect can be dramatically higher in the additional image data compared to the first and second image data. In this manner, the embodiments described herein may be used to enhance the detectability of DOI for wafer inspection systems using information from multiple optical states.

Figure 3:
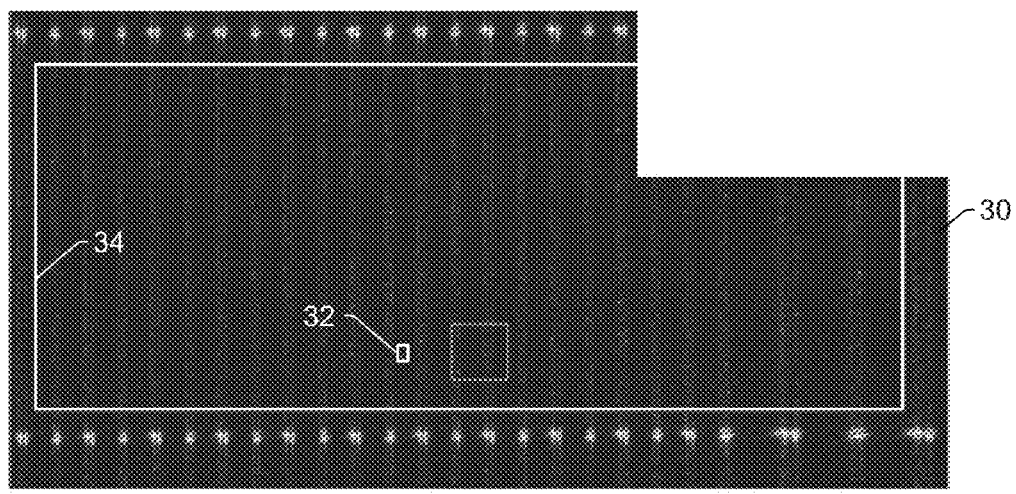
FIG. 3 includes different output generated for the same location on a wafer using the different optical states of FIG. 1.
Figure 3:
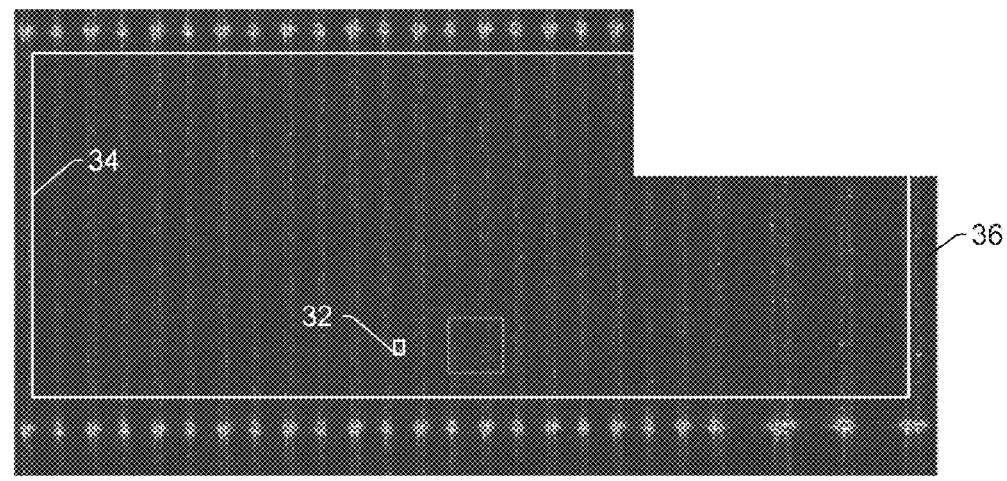
Figure 4:
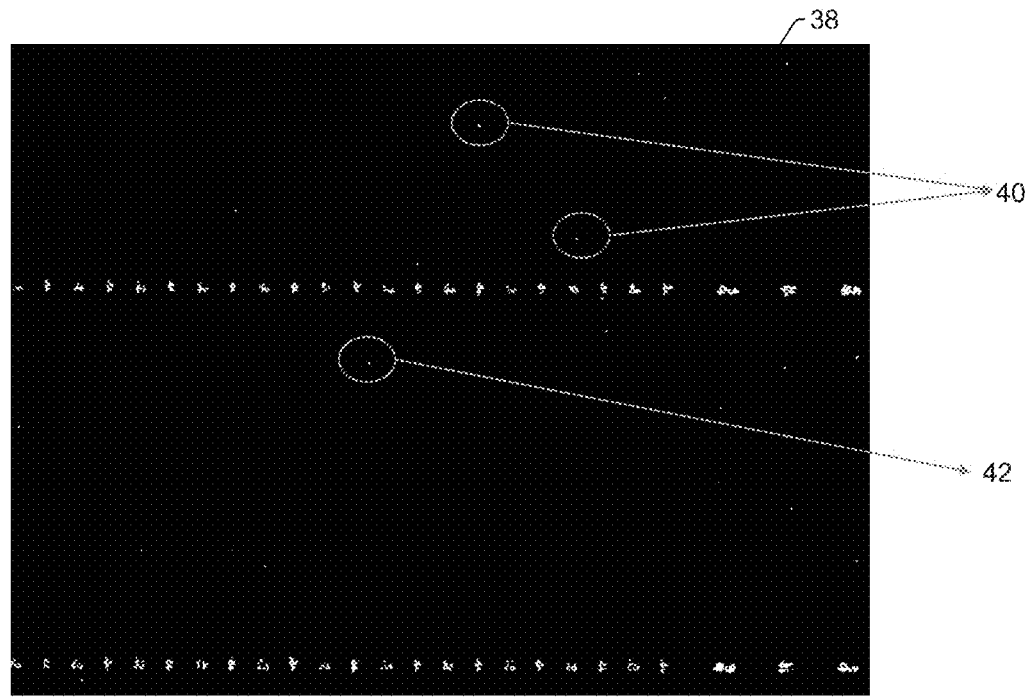
FIG. 4 is image data generated using one example of the output of FIG. 3.
Figure 5:
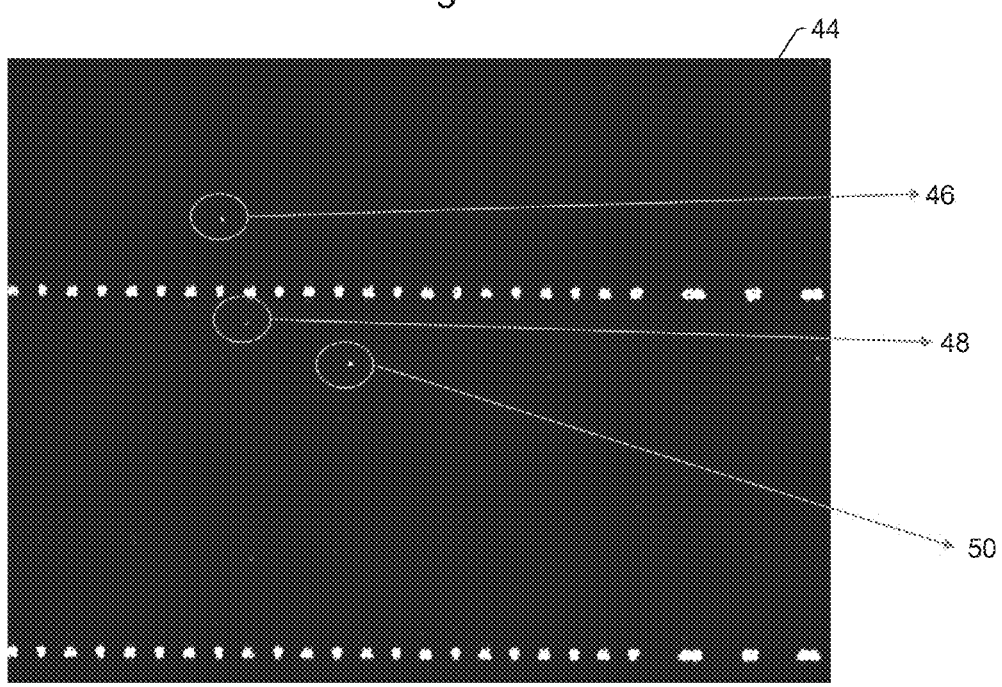
FIG. 5 is additional image data created by combining the image data of FIG. 4 with other image data generated using the other example of the output of FIG. 3.

An example of how the S/N of a defect can be improved is shown in FIGS. 3-5. In particular, output 30 shown in FIG. 3 is a raw image of a bridge defect from an azimuthal angle of 45 degrees. The S/N (max Diff) of the bridge defect was 1.265 in this image. The S/N was determined using the signal in signal window 32 and the noise in noise window 34, which includes noise from page breaks. Output 36 shown in FIG. 3 is a raw image of the bridge defect from an azimuthal angle of −45 degrees. The S/N (max Diff) of the bridge defect was 1.051 in this image. The S/N was determined using the same signal window and noise window as described above. In this manner, the raw images of the bridge defect from azimuthal angles of 45 degrees and −45 degrees show that neither image has a sufficient S/N such that the defect can be captured using either image. For example, the S/Ns for the defect are 1.265 and 1.051, which are both much less than the typical threshold value used for defect detection.

FIG. 4 is an example of image data for the wafer generated using one of the raw images of FIG. 3. For example, image data 38 shown in FIG. 4 is image data generated by die-to-die subtraction and background suppression performed using one of the images shown in FIG. 3 and a corresponding reference image from an adjacent die on the wafer. As shown in FIG. 4, speckle noise appears as many nuisances in this image data. In this manner, speckle noise shows as many nuisances even after die-to-die subtraction and background suppression. In particular, with the background reduced, nuisance is still apparent in the image data. More specifically, signals 40 in image data 38 correspond to nuisance from speckle on a page break, while signal 42 corresponds to a defect. Therefore, the detectability of the defect will be reduced by the nuisance that remains after die-to-die subtraction and background suppression.

FIG. 5 is an example of additional image data created by combining the image data of FIG. 4 with other image data generated for the wafer using the other image of FIG. 3. In particular, image data 44 shown in FIG. 5 was created by performing image correlation using image data 38 and other image data, image data that was generated from output that was generated using a 45 degree azimuthal angle and image data that was generated from output that was generated using a −45 degree azimuthal angle. After correlation performed using the 45 degree azimuthal angle difference image data and the −45 degree azimuthal angle difference image data, the S/N of the defect in the image data created by image correlation is 2. In this manner, the S/N of the defect increases from 1.265 and 1.051 to 2. As such, the defect is now detectable with noise greatly reduced. For example, as shown in FIG. 5, peak noise 46 is the only speckle peak in the image data, which corresponds to noise that was present in both of the difference image data that was correlated. Peak noise 46 has a gray level of 1044. Second peak noise 48 has a gray level of 171. In contrast, defect 50 has a gray level of 2060. Therefore, the defect becomes detectable using the correlated image data. In this manner, the embodiments have been shown to detect a defect that is not detectable using either optical state alone (e.g., using image data from one illumination angle).

As described above, variation of illumination may be used to change the speckle pattern in image data of the wafer thereby reducing speckle noise after image correlation performed using that image data. In addition, although some embodiments are described above as using two illumination angles that are defined by a 45 degree azimuthal angle and a −45 degree azimuthal angle for the first and second optical states, the different optical states can be extended to various illumination angles, including changing azimuthal angles and/or elevation angles. Output for each of the different illumination angles may be acquired in different passes of the wafer. Correlating image data generated using more than two various illumination angles can be used to further suppress the noise and improve the S/N. For example, besides changing the azimuthal angles of illumination, changing elevation angle can also vary the speckle pattern greatly thereby increasing the un-correlation of noise and further improving the S/N. In this manner, performing the method using any additional optical state may help to further eliminate the un-correlated speckle noise and improve the S/N for defects on the wafer. In a similar manner, the correlation can be extended for any channel and any optical state.

As described above, speckle noise in wafer inspection systems (e.g., laser-based wafer inspection systems) is one of the main limitations on DOI detection ability. For example, speckle noise increases the noise level in inspection image data and reduces S/Ns. Therefore, speckle noise from wafer surface roughness may be one of the main limitations on achievable defect capture rates in some inspection systems. In addition, nuisance detected as a result of wafer noise (e.g., speckle-like noise from wafer roughness) is one of the major limitations on DOI detect ability. In particular, relatively high nuisance rates and wafer noise on "rough" wafers such as grainy metal etch wafers may limit the performance of inspection systems that otherwise have relatively good optical resolution. In addition, as wafer design rules continue to shrink, optical inspection systems preferably use shorter wavelengths and larger collection numerical apertures (NAs). Speckle noise consequently becomes a more dominant noise source.

However, as described above, combining the first image data and the second image data suppresses speckle noise in the additional image data created by the combining step. As such, the methods described herein can be used to reduce nuisance rates and to improve defect capture rates in wafer inspection systems by reducing a main limiting noise factor, namely speckle noise (e.g., caused by wafer surface roughness). Therefore, the embodiments described herein can be used to increase the sensitivity of wafer inspection systems. In addition, as described above, the embodiments described herein allow preservation of illumination coherence while reducing speckle noise thereby enabling the usage of Fourier filtering and improving the S/N.

In one embodiment, the method includes detecting defects on the wafer using the first image data, detecting defects on the wafer using the second image data, and reporting the defects detected on the wafer as a combination of the defects detected using any of the first image data, the second image data, and the additional image data. For example, defects are detected as described above using the additional image data. In a similar manner, defect detection may be separately performed using the first image data and the second image data. Defect detection performed separately using each of the different image data may be performed in substantially the same manner (e.g., using the same threshold value(s)). In this manner, the method may include detecting three sub-populations of defects (i.e., defects detected using the first image data, defects detected using the second image data, and defects detected using the additional image data). The three-sub-populations may then be combined to generate the defect population for the wafer. For example, the defect sub-populations may be combined using an OR function based on the image data in which the defect was detected. Any defects that are detected at substantially the same position in any two or more of the image data may be reported only once to avoid double reporting of any one defect. In this manner, any one defect that is detected in two different image data may be reported only once. The defects detected on the wafer may otherwise be reported in any suitable manner.

As described above, the method may also include generating different additional image data. That different additional image data may also be used for defect detection as described above. Any defects detected using that different additional image data may be combined with defects detected using any other image data (e.g., the additional image data, the first image data, the second image data, etc.) as described herein. Furthermore, if the wafer is scanned using more than two different optical states of the inspection system, image data generated using the output from the third, fourth, etc. optical states may also be used for defect detection, and any defects detected using that image data may be combined with defects detected using other image data (e.g., the additional image data, the first image data, the second image data, etc.) as described herein.

As described above, a defect that is not detectable in either of the first and second optical states may become detectable in the additional image data created by image correlation. In this manner, the additional image data may be used to detect defects on the wafer that are unique in that they are not or cannot be detected using either the first or second image data. As such, the defects detected using the additional image data may be used to supplement the inspection results with defects that were not or could not be detected by either optical state individually.

The embodiments described herein may also include defect feature level fusion across multiple optical states, which may provide opportunities for enhancement of separation between DOI and nuisances although both may have relatively high S/Ns. For example, in one embodiment, the method includes determining values for features of the defects using the additional image data. In this manner, "cross-optical state" features of defects can be determined by performing feature calculations based on fused image data. The defect features that are determined using the additional image data may include any suitable defect features, which may be determined in any suitable manner. In this manner, the additional image data may be treated as any other image data when it comes to defect feature determination.

In another embodiment, the method includes determining values for features of the defects using some combination of the first image data, the second image data, and the additional image data. In this manner, the "cross-optical state" features can be determined using method(s) and/or algorithm(s) similar to those used to determine "cross-channel" features. For example, defect features may be determined separately using different image data corresponding to the different optical states. Those defect features may then be combined to determine a different defect feature for the defect. For example, the values for defect features determined separately using different image data corresponding to different optical states may be combined into a new value for the defect feature. In another example, different defect features may be determined for a defect from different image data corresponding to different optical states. Those different defect features may then be used in some combination to determine another defect feature for the defect. The manner in which the different image data is used to determine the defect features may vary depending on the defects for which the features are being determined, the features that are being determined, and the image data itself (e.g., characteristics of the image data that may affect if or how well a feature can be determined using the image data). In this manner, values for features of the defects may be determined using all of the information that is available or some subset of the information that is available.

Nuisance filtering can be performed not only in the dimension of each individual optical state, but in the n-dimensional space generated by the multiple optical states, which provides more possibilities for identifying separations between nuisances and DOI. For example, in one embodiment, detecting the defects includes identifying potential defects on the wafer using the additional image data and identifying the defects by performing nuisance filtering of the potential defects using pixel level information about the potential defects determined using the first image data, the second image data, the additional image data, or some combination thereof. Therefore, nuisance filtering can be performed by combining the information at the pixel level across multiple optical states (multiple passes), which creates more potential for performance. The potential defects may be identified in the additional image data by defect detection, which may be performed as described herein. Nuisance filtering as described above may also be performed for potential defects identified using any other image data described herein.

In another embodiment, detecting the defects includes identifying potential defects on the wafer using the additional image data and identifying the defects by performing nuisance filtering of the potential defects using values for features of the potential defects determined using the first image data, the second image data, the additional image data, or some combination thereof. Therefore, nuisance filtering can be performed by combining information at the feature level across multiple optical states (e.g., multiple passes), which creates more potential for performance. Identifying the potential defects using the additional image data may be performed as described above. The values for the features of the potential defects may include any of the values of any of the features described herein and may be determined as described herein. Nuisance filtering as described above may also be performed for potential defects identified using any other image data described herein.

The embodiments described herein may also include image fusion and binning for wafer inspection systems. Binning can be performed not only in the dimension of each individual optical state, but also in the n-dimensional space generated by the multiple optical states, which provides more possibilities for finding separations between different types of defects. For example, in one embodiment, the method includes binning the defects using pixel level information about the defects determined using the first image data, the second image data, the additional image data, or some combination thereof. Therefore, binning, the defects may be performed by combining, information at the pixel level across multiple optical states (e.g., multiple passes), which creates more potential for performance.

In another embodiment, the method includes binning the defects using values for features of the defects determined using the first image data, the second image data, the additional image data, or some combination thereof. Therefore, binning the defects may be performed by combining information at the defect feature level across multiple optical states (e.g., multiple passes), which creates more potential for performance. The values for the features of the defects determined using the first image data, the second image data, the additional image data, or some combination thereof may be determined as described further herein.

As described above, different additional image data may be generated for a wafer by combining image data corresponding to different combinations of optical states of an inspection system. In other words, different fused image data may be generated for a water. The different fused image data may be used in all of the steps described herein in the same manner as the additional image data. In addition, if different fused image data is generated for a wafer, that different fused image data may be used to determine an appropriate or optimal inspection recipe for a wafer. For example, the different fused image data may be used independently for defect detection, which may be performed as described herein. The defects that are detected using the different fused image data may then be compared. The defects that are uniquely detected using the different fused image data as compared to the individual optical states may be reviewed by defect review to determine which fused image data detected the most unique DOI. That same fused image data may then be created for other wafers of the same process and/or layer and used for detecting defects on those wafers. In this manner, one or more parameters of an inspection recipe may be determined experimentally using the fused image data (i.e., using fused image data generated from experimentally acquired output for a wafer). In addition, the multiple optical states used in the methods described herein may be determined in this manner using a defect detection method or algorithm (e.g., the defect detection algorithm in the inspection recipe). As such, the algorithm may be used to perform mode selection for an inspection recipe.

Such an approach to determining one or more parameters of an inspection recipe may be used to determine the two or more optical states that can advantageously be used in the methods described herein for a predetermined defect detection method or algorithm. However, such an approach to determining one or more parameters of an inspection recipe may also be used to determine one or more defect detection parameters (e.g., a defect detection method or algorithm) that should be used with the two or more optical states. In this manner, the fused image data may be used to determine any parameter(s) of an inspection recipe.

As described above, the image data that is fused may be generated from output generated using different optical states of a single inspection system. However, the methods described herein are not limited to just fusing image data that is generated from output generated using different optical states of a single inspection system. For example, in addition or alternatively, the image data that is fused may include image data generated from output acquired in different passes (i.e., scans) but with the same optical state. In one such embodiment, generating the output as described above using first and second optical states of the inspection system is performed in one pass. In this embodiment, the method also includes generating additional output for the wafer by scanning the wafer in a different pass with the inspection system using the first or second optical state of the inspection system. In this manner, output using the same (first or second) optical state may be generated in different passes of the wafer performed by the inspection system. Generating the additional output may be further performed as described herein.

Such a method may also include generating different image data for the wafer using the additional output generated in the different pass. Generating the different image data may be performed as described further herein. In addition, such a method may include combining the different image data with the first image data if the different pass is performed using the first optical state or the second image data if the different pass is performed using the second optical state corresponding to substantially the same locations on the wafer thereby creating further additional image data for the wafer. In this manner, the combining step may be performed using the image data acquired in different passes but with the same optical state. This combining step may be further performed as described herein.

Such a method may further include detecting defects on the wafer using the further additional image data. Detecting the defects on the wafer using the further additional image data may be performed as described further herein. Such methods may also include any other step(s) described herein.

Additional methods may include fusing image data, that corresponds to different passes of the wafer performed using the same optical state of an inspection system. For example, another embodiment relates to a different method for detecting defects on a wafer. This method includes generating output for a wafer by scanning the wafer with an inspection system in first and second passes using a first optical state of the inspection system. Generating the output in this step may be performed as described further herein. The first optical state may include any of the optical states described herein.

This method also includes generating first image data for the wafer using the output generated in the first pass and second image data for the wafer using the output generated in the second pass. Generating the first and second image data in this step may be performed as described further herein. The first and second image data may include any of the image data described herein.

This method further includes combining the first image data and the second image data corresponding to substantially the same locations on the wafer thereby creating additional image data for the wafer. Combining the first image data and the second image data in this step may be performed as described further herein. The additional image data ma include any of the additional image data described herein. In addition, the method includes detecting defects on the wafer using the additional image data. Detecting the defects on the wafer in this step may be performed as described further herein. This method may include any other step(s) described herein.

Fusing image data from the same optical state but from different passes may be particularly useful for cases in which the image data is dominated by random noise. For example, if image data is generated using output generated in a first pass using one optical state and fused with image data generated using output generated in a second pass using the same optical state, all random noise sources may be substantially eliminated in the fused image data, while ensuring coincidence of the signal from DOI. In addition, as described above, different image data corresponding to the same optical state can be fused independently. In other words, first and second image data corresponding to the same optical state does not need to be combined with image data corresponding to an already fused optical state (corresponding to a different optical state).

Furthermore, in addition or alternatively, the method may be performed using output generated by different inspection systems. For example, in one embodiment, the method includes generating output for the wafer by scanning the wafer with a different inspection system. Generating the output for the wafer with the different inspection system may be performed as described herein. The different inspection system may be a DF or BF system. For example, the inspection system may be a DF system, and the different inspection system may be a BF system. In another example, the inspection system may be a DF system, and the different inspection system may be a different DF system (e.g., a DF system having a different configuration than the inspection system). The different inspection systems may be configured as described herein or may have any other suitable configuration known in the art.

Such a method may also include generating third image data for the wafer using the output generated using the different inspection system. Generating the third image data may be performed according to any of the embodiments described herein. In addition, such a method may include combining the third image data with the first or second image data corresponding to substantially the same locations on the wafer thereby creating further additional image data for the wafer. Combining the third image data with the first or second image data may be performed in this embodiment according to any of the embodiments described herein. Such a method may further include detecting defects on the wafer using the further additional image data. Detecting the defects on the wafer using the further additional image data may be performed as described further herein. Such an embodiment may include any other step(s) described herein. In this manner, the method may include using output collected from different inspection systems and fusing image data generated using the output collected from the different inspection systems.

In another embodiment, a method for detecting defects on a wafer includes generating output for a wafer by scanning the wafer with first and second inspection systems. Generating the output for the wafer in this step may be performed as described further herein. The first and second inspection systems may include any of the different inspection systems described herein. Scanning the wafer with the first and second inspection systems may be performed using the same or substantially the same optical state. Alternatively, scanning the wafer with the first and second inspection systems may be performed using different optical states. In this manner, the different optical states corresponding to the different image data that is fused may be different optical states of different inspection systems. For example, image data corresponding to optical state A of inspection system X can be combined as described further herein with image data corresponding to optical state B of inspection system Y. Optical states A and B can be identical or different. The same or substantially the same optical state and the different optical states may include any of the optical states described herein. The method also includes generating first image data for the wafer using the output generated using the first inspection system and second image data for the wafer using the output generated using the second inspection system. Generating the first and second image data may be performed as described further herein. The first and second image data may include any of the image data described herein.

The method further includes combining the first image data and the second image data corresponding to substantially the same locations on the wafer thereby creating additional image data for the wafer. This combining step may be performed as described further herein. In addition, the method includes detecting defects on the wafer using the additional image data. Detecting the defects on the wafer in this step may be performed as described further herein.

As described above, the method may include generating output using different inspection systems and generating different image data using the output generated using the different inspection systems. However, the method may not necessarily include generating the output using all of the different inspection systems. For example, the output generated using one or more of the different inspection systems may be acquired from one or more storage media in which the output has been stored (e.g., by the one or more different inspection systems). The acquired output generated using the different inspection systems may then be used as described further herein. In this manner, the methods described herein can perform image fusion regardless of the origin of the output used to generate the image data that is fused.

In addition, the output generated by the different inspection systems that is used in the embodiments described herein may necessarily be generated using different optical states (as would be the case if the different inspection systems include a DF inspection system and a BF inspection system or DF inspection systems having completely different (e.g., non-overlapping) configurations). However, the output generated by the different inspection systems that is used in the embodiments described herein may be generated using the same optical state or substantially the same optical state (as may be the case if the different inspection systems include two inspection systems having the same configuration or relatively similar configurations).

The embodiments described herein may also include storing results of one or more steps of one or more methods described herein in a storage medium. The results may include any of the results described herein. The results may be stored in any manner known in the art. The storage medium may include any suitable storage medium known in the art. After the results have been stored, the results can be accessed in the storage medium and used by any of the method or system embodiments described herein, any other method, or any other system. Furthermore, the results may be stored "permanently," "semi-permanently," temporarily, or for some period of time. For example, the storage medium may be random access memory (RAM), and the results may not necessarily persist indefinitely in the storage medium.

Figure 6:
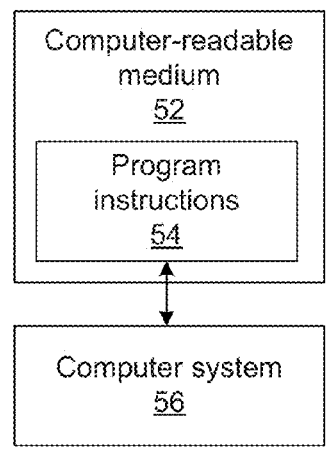
FIG. 6 is a block diagram illustrating one embodiment of a computer-readable medium that includes program instructions executable on a computer system for performing a computer-implemented method for detecting defects on a wafer.

Another embodiment relates to a computer-readable medium that includes program instructions executable on a computer system for performing a computer-implemented method for detecting defects on a wafer. One such embodiment is shown in FIG. 6. For example, as shown in FIG. 6, computer-readable medium 52 includes program instructions 54 executable on computer system 56 for performing a computer-implemented method for detecting defects on a wafer.

The computer-implemented method includes acquiring output for a wafer generated by scanning the wafer with an inspection system using first and second optical states of the inspection system. The first and second optical states are defined by different values for at least one optical parameter of the inspection system. The first and second optical states may include any of the optical states described herein. The different values for the at least one optical parameter of the inspection system may include any of the different values described herein. The at least one optical parameter of the inspection system may include any of the optical parameters described herein. The inspection system may include any of the inspection systems described herein.

Acquiring the output generated for the wafer may be performed using the inspection system. For example, acquiring the output may include using the inspection system to scan light over the wafer and to generate output responsive to light scattered from the wafer detected by the inspection system during scanning. In this manner, acquiring the output may include scanning the wafer. However, acquiring the output does not necessarily include scanning the wafer. For example, acquiring the output may include acquiring the output from a storage medium in which the output has been stored (e.g., by the inspection system). Acquiring the output from the storage medium may be performed in any suitable manner, and the storage medium from which the output is acquired may include any of the storage media described herein. The output may include any of the output described herein.

The computer-implemented method also includes generating first image data for the wafer using the output generated using the first optical state and second image data for the wafer using the output generated using the second optical state. Generating the first image data and the second image data may be performed as described further herein. The first and second image data may include any such image data described herein.

The computer-implemented method further includes combining the first image data and the second image data corresponding to substantially the same locations on the wafer thereby creating additional image data for the wafer. Combining the first image data and the second image data may be performed as described further herein. The additional image data may include any of the additional image data described herein. In addition, the method includes detecting defects on the wafer using the additional image data. Detecting the defects on the wafer may be performed as described further herein. The defects detected on the wafer may include any of the defects described herein. The computer-implemented method for which the program instructions are executable may include any other step(s) of any other method(s) described herein.

Program instructions 54 implementing methods such as those described herein may be transmitted over or stored on computer-readable medium 52. The computer-readable medium may be a storage medium such as a read-only memory, a RAM, a magnetic or optical disk, or a magnetic tape or any other suitable computer-readable medium known in the art.

The program instructions may be implemented in any of various ways, including procedure-based techniques, component-based techniques, and/or object-oriented techniques, among others. For example, the program instructions may be implemented using Matlab, Visual Basic, ActiveX controls, C, C++ objects, C#, JavaBeans, Microsoft Foundation Classes ("MFC"), or other technologies or methodologies, as desired.

Computer system 56 may take various forms, including a personal computer system, mainframe computer system, workstation, system computer, image computer, programmable image computer, parallel processor, or any other device known in the art. In general, the term "computer system" may be broadly defined to encompass any device having one or more processors, which executes instructions from a memory medium.

Figure 7:
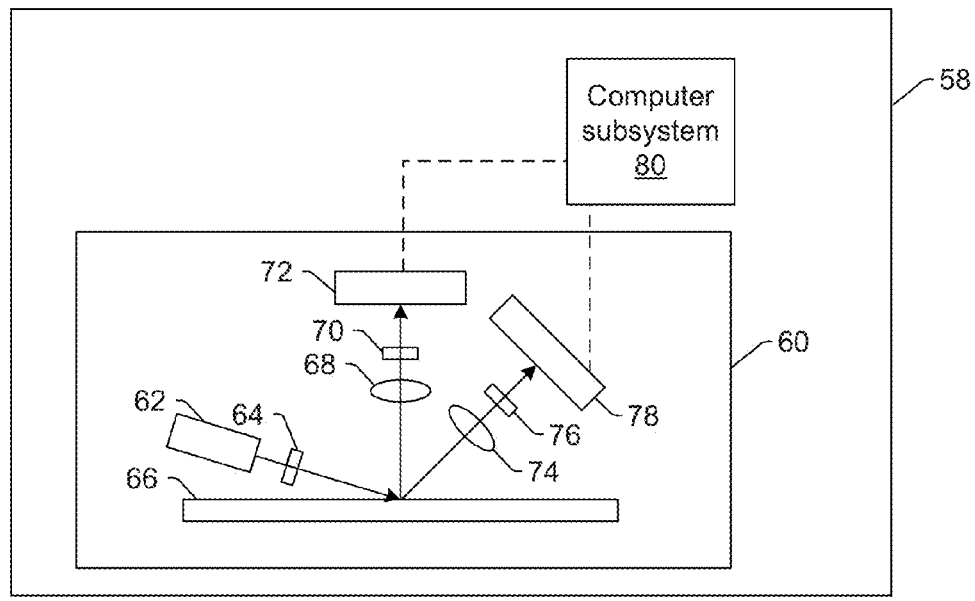
FIG. 7 is a schematic diagram illustrating a side view of one embodiment of a system configured to detect defects on a wafer.

An additional embodiment relates to a system configured to detect defects on a wafer. One embodiment of such a system is shown in FIG. 7. As shown in FIG. 7, system 58 includes inspection subsystem 60 and computer subsystem 80. The inspection subsystem is configured to generate output for a wafer by scanning the wafer using first and second optical states of the inspection subsystem. For example, as shown in FIG. 7, the inspection subsystem includes light source 62. Light source 62 may include any suitable light source known in the art such as a laser. Light source 62 is configured to direct light to polarizing component 64, which may include any suitable polarizing component known in the art. In addition, the inspection subsystem may include more than one polarizing component (not shown), each of which may be positioned independently in the path of the light from the light source. Each of the polarizing components may be configured to alter the polarization of the light from the light source in a different manner. The inspection subsystem may be configured to move the polarizing components into and out of the path of the light from the light source in any suitable manner depending on which polarization setting is selected for illumination of the wafer during a scan. The polarization setting used for the illumination of the wafer during a scan may include P, S, or circularly polarized (C).

Light exiting polarizing component 64 is directed to wafer 66 at an oblique angle of incidence, which may include any suitable oblique angle of incidence. The inspection subsystem may also include one or more optical components (not shown) that are configured to direct light from light source 62 to polarizing component 64 or from polarizing component 64 to wafer 66. The optical components may include any suitable optical components known in the art such as, but not limited to, a reflective optical component. In addition, the light source, the polarizing component, and/or the one or more optical components may be configured to direct the light to the wafer at one or more angles of incidence (e.g., an oblique angle of incidence and/or a substantially normal angle of incidence). The inspection subsystem may be configured to perform the scanning by scanning the light over the wafer in any suitable manner.

Light scattered from wafer 66 may be collected and detected by multiple channels of the inspection subsystem during scanning. For example, light scattered from wafer 66 at angles relatively close to normal may be collected by lens 68. Lens 68 may include a refractive optical element as shown in FIG. 7. In addition, lens 68 may include one or more refractive optical elements and/or one or more reflective optical elements. Light collected by lens 68 may be directed to polarizing component 70, which may include any suitable polarizing component known in the art. In addition, the inspection subsystem may include more than one polarizing component (not shown), each of which may be positioned independently in the path of the light collected by the lens. Each of the polarizing components may be configured to alter the polarization of the light collected by the lens in a different manner. The inspection subsystem may be configured to move the polarizing components into and out of the path of the light collected by the lens in any suitable manner depending on which polarization setting is selected for detection of the light collected by lens 68 during scanning. The polarization setting used for the detection of the light collected by lens 68 during scanning may include any of the polarization settings described herein (e.g., P, S, and N).

Light exiting polarizing component 70 is directed to detector 72. Detector 72 may include any suitable detector known in the art such as a charge coupled device (CCD) or another type of imaging detector. Detector 72 is configured to generate output that is responsive to the scattered light collected by lens 68 and transmitted by polarizing component 70 if positioned in the path of the collected scattered light. Therefore, lens 68, polarizing component 70 if positioned in the path of the light collected by lens 68, and detector 72 form one channel of the inspection subsystem. This channel of the inspection subsystem may include any other suitable optical components (not shown) known in the art such as a Fourier filtering component.

Light scattered from wafer 66 at different angles may be collected by lens 74. Lens 74 may be configured as described above. Light collected by lens 74 may be directed to polarizing component 76, which may include any suitable polarizing component known in the art. In addition, the inspection subsystem may include more than one polarizing component (not shown), each of which may be positioned independently in the path of the light collected by the lens. Each of the polarizing components may be configured to alter the polarization of the light collected by the lens in a different manner. The inspection subsystem may be configured to move the polarizing components into and out of the path of the light collected by the lens in any suitable manner depending on which polarization setting is selected for detection of the light collected by lens 74 during scanning. The polarization setting used for detection of the light collected by lens 74 during scanning may include P, S, or N.

Light exiting polarizing component 76 is directed to detector 78, which may be configured as described above. Detector 78 is also configured to generate output that is responsive to the collected scattered light that passes through polarizing component 76 if positioned in the path of the scattered light. Therefore, lens 74, polarizing component 76 if positioned in the path of the light collected by lens 74, and detector 78 may form another channel of the inspection subsystem. This channel may also include any other optical components (not shown) described above. In some embodiments, lens 74 may be configured to collect light scattered from the wafer at polar angles from about 20 degrees to about 70 degrees. In addition, lens 74 may be configured as a reflective optical component (not shown) that is configured to collect light scattered from the wafer at azimuthal angles of about 360 degrees.

The inspection subsystem shown in FIG. 7 may also include one or more other channels (not shown). For example, the inspection subsystem may include an additional channel, which may include any of the optical components described herein such as a lens, one or more polarizing components, and a detector, configured as a side channel. The lens, the one or more polarizing components, and the detector may be further configured as described herein. In one such example, the side channel may be configured to collect and detect light that is scattered out of the plane of incidence (e.g., the side channel may include a lens, which is centered in a plane that is substantially perpendicular to the plane of incidence, and a detector configured to detect light collected by the lens).

The first and second optical states are defined by different values for at least one optical parameter of the inspection subsystem. The first and second optical states may be defined by any of the different values for any of the optical parameters of the inspection subsystem described herein. In addition, the values of any of the optical parameters may be altered in any suitable manner if necessary between passes. For example, if the different values are different values of illumination polarization states, between passes polarizing component 64 may be removed and/or replaced as described herein with a different polarizing component. In another example, if the different values are different angles, the position of the light source and/or any other optical components (e.g., polarizing component 64) used to direct the light to the wafer may be altered between passes in any suitable manner.

Output generated by the detectors during scanning may be provided to computer subsystem 80. For example, the computer subsystem may be coupled to each of the detectors (e.g., by one or more transmission media shown by the dashed lines in FIG. 7, which may include any suitable transmission media known in the art) such that the computer subsystem may receive the output generated by the detectors. The computer subsystem may be coupled to each of the detectors in any suitable manner. The output generated by the detectors during scanning of the wafer may include any of the output described herein.

The computer subsystem is configured to generate first image data for the wafer using the output generated using the first optical state and second image data for the wafer using the output generated using the second optical state. The computer subsystem may be configured to generate the first image data and the second image data according to any of the embodiments described herein. The first image data and the second image data may include any such image data described herein.

The computer subsystem is also configured to combine the first image data and the second image data corresponding to substantially the same locations on the wafer thereby creating additional image data for the wafer. The computer subsystem may be configured to combine the first and second image data according to any of the embodiments described herein. The additional image data may include any of the additional image data described herein.

The computer subsystem is further configured to detect defects on the wafer using the additional image data. The computer subsystem may be configured to detect the defects according to any of the embodiments described herein. The defects may include any of the defects described herein.

The computer subsystem may be configured to perform any other step(s) of any method embodiment(s) described herein. The computer subsystem may be further configured as described herein. The inspection subsystem may also be further configured as described herein. Furthermore, the system may be further configured as described herein.

It is noted that FIG. 7 is provided herein to generally illustrate one configuration of an inspection subsystem that may be included in the system embodiments described herein. Obviously, the inspection subsystem configuration described herein may be altered to optimize the performance of the inspection subsystem as is normally performed when designing a commercial inspection system. In addition, the systems described herein may be implemented using an existing inspection system by adding functionality described herein to an existing inspection system) such as the Puma 9000 and 91xx series of tools that are commercially available from KLA-Tencor. For some such systems, the methods described herein may be provided as optional functionality of the system (e.g., in addition to other functionality of the system). Alternatively, the system described herein may be designed "from scratch" to provide a completely new system.

Further modifications and alternative embodiments of various aspects of the invention may be apparent to those skilled in the art in view of this description. For example, systems and methods for detecting defects on a wafer are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for detecting defects on a wafer, comprising:
    generating output for a wafer by scanning the wafer with an inspection system in first and second passes using a first optical state of the inspection system;
    generating first image data for the wafer using the output generated in the first pass and second image data for the wafer using the output generated in the second pass;
    combining the first image data and the second image data corresponding to substantially the same locations on the wafer thereby creating additional image data for the wafer;
    detecting defects on the wafer using the additional image data; and
    generating output for the wafer by scanning the wafer with a different inspection system, generating third image data for the wafer using the output generated using the different inspection system, combining the third image data with the first or second image data corresponding to substantially the same locations on the wafer thereby creating further additional image data for the wafer, and detecting defects on the wafer using the further additional image data.

2. The method of claim 1, wherein scanning the wafer with the inspection system using the first optical state is performed with coherent light.

3. The method of claim 1, further comprising generating additional output for the wafer by scanning the wafer in a different pass with the inspection system using a second optical state of the inspection system, generating different image data for the wafer using the additional output generated in the different pass, combining the different image data with the first or second image data corresponding to substantially the same locations on the wafer thereby creating other additional image data for the wafer, and detecting defects on the wafer using the other additional image data.

4. The method of claim 1, wherein the first and second image data comprises difference image data.

5. The method of claim 1, wherein said combining comprises performing image correlation on the first image data and the second image data corresponding to substantially the same locations on the wafer.

6. The method of claim 1, wherein said combining is performed at the pixel level of the first and second image data.

7. The method of claim 1, wherein defect detection is not performed prior to the combining step.

8. The method of claim 1, wherein portions of the additional image data that correspond to the defects have greater signal-to-noise ratios than portions of the first and second image data that are combined to create the portions of the additional image data.

9. The method of claim 1, wherein the additional image data has less noise than the first and second image data.

10. The method of claim 1, wherein the additional image data has less speckle noise than the first and second image data.

11. The method of claim 1, further comprising detecting defects on the wafer using the first image data, detecting defects on the wafer using the second image data, and reporting the defects detected on the wafer as a combination of the defects detected using any of the first image data, the second image data, and the additional image data.

12. The method of claim 1, further comprising determining values for features of the defects using the additional image data.

13. The method of claim 1, further comprising determining values for features of the defects using some combination of the first image data, the second image data, and the additional image data.

14. The method of claim 1, wherein detecting the defects comprises identifying potential defects on the wafer using the additional image data and identifying the defects by performing nuisance filtering of the potential defects using pixel level information about the potential defects determined using the first image data, the second image data, the additional image data, or some combination thereof.

15. The method of claim 1, wherein detecting the defects comprises identifying potential defects on the wafer using the additional image data and identifying the defects by performing nuisance filtering of the potential defects using values for features of the potential defects determined using the first image data, the second image data, the additional image data, or some combination thereof.

16. The method of claim 1, further comprising binning the defects using pixel level information about the defects determined using the first image data, the second image data, the additional image data, or some combination thereof.

17. The method of claim 1, further comprising binning the defects using values for features of the defects determined using the first image data, the second image data, the additional image data, or some combination thereof.

* * * * *